(12) United States Patent
Thornton

(10) Patent No.: US 7,721,741 B2
(45) Date of Patent: May 25, 2010

(54) ORAL APPLIANCE FOR TREATING A BREATHING CONDITION

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 0 days.

(21) Appl. No.: 12/470,963

(22) Filed: May 22, 2009

(65) Prior Publication Data
US 2009/0223525 A1 Sep. 10, 2009

Related U.S. Application Data

(63) Continuation of application No. 11/278,918, filed on Apr. 6, 2006.

(51) Int. Cl.
*A61F 11/00* (2006.01)
*A61C 5/14* (2006.01)
*A61C 3/00* (2006.01)
*A61C 9/00* (2006.01)
(52) U.S. Cl. .................. 128/848; 128/857; 128/859; 128/861; 433/18; 433/19; 433/24; 433/37; 433/41; 433/42
(58) Field of Classification Search .................. 128/857, 128/859, 861; 433/18–19, 24, 37, 41, 42
See application file for complete search history.

(56) References Cited

U.S. PATENT DOCUMENTS

| 690,663 A | 1/1902 | Pratt |
| 746,869 A | 12/1903 | Moulton |

(Continued)

FOREIGN PATENT DOCUMENTS

| DE | 2 320 501 | 11/1974 |

(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner*—Patricia Bianco
*Assistant Examiner*—Brandon Jackson
(74) *Attorney, Agent, or Firm*—Baker Botts L.L.P.

(57) ABSTRACT

In certain embodiments, an apparatus for treating a breathing condition includes a body, a threaded member, a hook, and a receiver. The body comprises a front stop, a rear stop, and a guide extending between the stops. The threaded member couples between the stops and rotates relative to the body. The hook couples to the guide, comprises a threaded passage and an arm that engages a lower arch, and travels in a forward direction along the guide to adjust the position of the lower arch. The receiver couples to the lower arch and comprises a shelf that engages the arm of the hook. The apparatus may include an extender coupled to the receiver and providing a shelf that is more rearward than the shelf of the receiver. The apparatus may include a post that couples the apparatus to another device. In certain embodiments, a removable receiver, which may be one of a plurality of removable receivers with different dimensions, is removably positioned within a recess in a posterior surface of a lower arch and is engaged by a connector of an upper arch to define the relative positions of the arches.

12 Claims, 15 Drawing Sheets

U.S. PATENT DOCUMENTS

| | | |
|---|---|---|
| 774,446 A | 11/1904 | Moulton |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,712,160 A | 7/1955 | Sterczek |
| 2,833,278 A | 5/1958 | Ross |
| 2,867,212 A | 1/1959 | Nunn, Jr. |
| 2,882,893 A | 4/1959 | Godfroy |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick et al. |
| 3,522,805 A | 8/1970 | Wallshein |
| 3,690,004 A | 9/1972 | Frush |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner et al. |
| 4,026,024 A | 5/1977 | Tradowsky |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud et al. |
| 4,289,127 A | 9/1981 | Nelson |
| 4,304,227 A | 12/1981 | Samelson |
| 4,376,628 A | 3/1983 | Aardse |
| 4,382,783 A | 5/1983 | Rosenberg |
| 4,433,956 A | 2/1984 | Witzig |
| 4,439,147 A | 3/1984 | Magill et al. |
| 4,439,149 A | 3/1984 | Devincenzo |
| 4,454,090 A | 6/1984 | Saumell |
| 4,495,945 A | 1/1985 | Liegner |
| 4,505,672 A | 3/1985 | Kurz |
| 4,530,662 A | 7/1985 | Andersson et al. |
| 4,553,549 A | 11/1985 | Pope et al. |
| 4,568,280 A | 2/1986 | Ahlin |
| 4,569,342 A | 2/1986 | von Nostitz |
| 4,593,686 A | 6/1986 | Lloyd et al. |
| 4,602,905 A | 7/1986 | O'Keefe, III |
| 4,639,220 A | 1/1987 | Nara et al. |
| 4,668,188 A | 5/1987 | Wolfenson et al. |
| 4,669,459 A | 6/1987 | Spiewak et al. |
| 4,676,240 A | 6/1987 | Gardy |
| 4,715,368 A | 12/1987 | George |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,862,903 A | 9/1989 | Campbell |
| 4,892,478 A | 1/1990 | Tateosian et al. |
| 4,901,737 A | 2/1990 | Toone |
| 4,932,867 A | 6/1990 | Ueno |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman et al. |
| 5,028,232 A | 7/1991 | Snow |
| 5,040,976 A | 8/1991 | Ubel, III et al. |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte et al. |
| 5,056,534 A | 10/1991 | Wright |
| 5,064,371 A | 11/1991 | Smeltzer |
| 5,066,231 A | 11/1991 | Oxman et al. |
| 5,078,600 A | 1/1992 | Austin |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| 5,154,184 A | 10/1992 | Alvarez |
| 5,154,609 A | 10/1992 | George |
| 5,183,057 A | 2/1993 | Syrop et al. |
| 5,188,529 A | 2/1993 | Lüth |
| 5,190,457 A | 3/1993 | Schreinemakers |
| 5,213,498 A | 5/1993 | Pelerin |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,365,945 A | 11/1994 | Halstrom |
| 5,370,533 A | 12/1994 | Bushnell |
| 5,373,859 A | 12/1994 | Forney |
| 5,409,017 A | 4/1995 | Lowe |
| 5,415,544 A | 5/1995 | Oxman et al. |
| 5,427,117 A | 6/1995 | Thornton |
| 5,503,552 A | 4/1996 | Diesso |
| 5,537,994 A | 7/1996 | Thornton |
| 5,551,872 A | 9/1996 | Mena |
| 5,562,449 A | 10/1996 | Jacobs et al. |
| 5,566,683 A | 10/1996 | Thornton |
| 5,582,517 A | 12/1996 | Adell |
| 5,678,567 A | 10/1997 | Thornton et al. |
| 5,681,164 A | 10/1997 | Bass |
| 5,718,244 A | 2/1998 | Thornton |
| 5,720,302 A | 2/1998 | Belfer |
| 5,755,219 A | 5/1998 | Thornton |
| 5,807,100 A | 9/1998 | Thornton |
| 5,829,441 A | 11/1998 | Kidd et al. |
| 5,846,082 A | 12/1998 | Thornton |
| 5,891,372 A | 4/1999 | Bessett et al. |
| 5,954,048 A | 9/1999 | Thornton |
| 5,983,892 A | 11/1999 | Thornton |
| 6,083,442 A | 7/2000 | Gabilly |
| 6,109,265 A | 8/2000 | Frantz et al. |
| 6,155,262 A | 12/2000 | Thornton et al. |
| 6,209,542 B1 | 4/2001 | Thornton |
| 6,247,926 B1 | 6/2001 | Thornton |
| 6,305,376 B1 | 10/2001 | Thornton |
| 6,318,997 B1 | 11/2001 | Mayweather |

| | | |
|---|---|---|
| 6,325,064 B1 | 12/2001 | Thornton |
| 6,374,824 B1 | 4/2002 | Thornton |
| 6,405,729 B1 | 6/2002 | Thornton |
| 6,464,924 B1 | 10/2002 | Thornton |
| 6,516,805 B1 | 2/2003 | Thornton |
| 6,571,798 B1 | 6/2003 | Thornton |
| 6,675,802 B1 | 1/2004 | Thornton |
| 6,845,774 B2 | 1/2005 | Gaskell |
| 6,857,428 B2 | 2/2005 | Thornton |
| 6,877,513 B2 | 4/2005 | Scarberry et al. |
| 7,174,895 B2 | 2/2007 | Thornton |
| 7,243,650 B2 | 7/2007 | Thornton |
| 7,597,103 B2 | 10/2009 | Thornton |
| 2004/0237965 A1 | 12/2004 | Bibi et al. |
| 2007/0125388 A1 | 6/2007 | Thornton et al. |
| 2007/0235037 A1 | 10/2007 | Thornton |
| 2007/0292819 A1 | 12/2007 | Scarberry et al. |
| 2008/0006273 A1 | 1/2008 | Thornton |
| 2008/0006274 A1 | 1/2008 | Thornton |
| 2008/0032256 A1 | 2/2008 | Thornton |

FOREIGN PATENT DOCUMENTS

| | | |
|---|---|---|
| DE | 29506512.5 | 7/1995 |
| EP | 0 312 368 A1 | 4/1989 |
| EP | 0 359 135 A1 | 3/1990 |
| GB | 1 569 129 | 6/1980 |
| GB | 2 072 567 A | 10/1981 |
| WO | WO 91/12777 | 9/1991 |
| WO | WO 98/26736 | 6/1998 |
| WO | WO 98/46177 | 10/1998 |

OTHER PUBLICATIONS

Photocopies of 2-piece dental device manufactured by Currie-Gibson Dental Lboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 4 pages, Unknown.

Great Lakes Orthodontics, Ltd.; *Nocturnal Airway Patency Applicance*; 2 pages, Not Dated.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

PCT Notification of Transmittal of the International Search Report or the Declaration for International Application No. PCT/US97/08708, 4 pages, Aug. 12, 1997.

PCT Invitation to Pay Additional Fees for International Application No. PCT/US03/13705, 5 pages, Oct. 10, 2003.

PCT International Search Report and Written Opinion, International Application No. PCT/US06/26622, 11 pages, Feb. 21, 2007.

PCT International Search Report and Written Opinion, International Application No. PCT/US07/02736, 10 pages, Oct. 26, 2007.

FIG. 4A
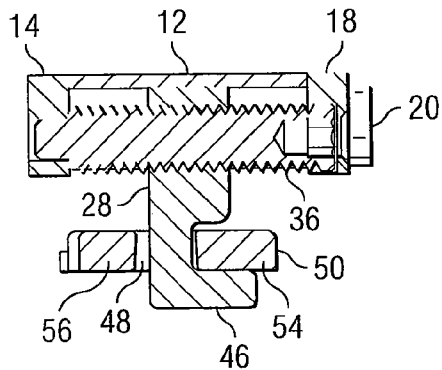
FIG. 4B
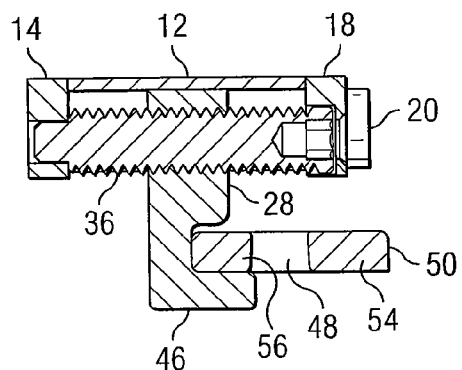
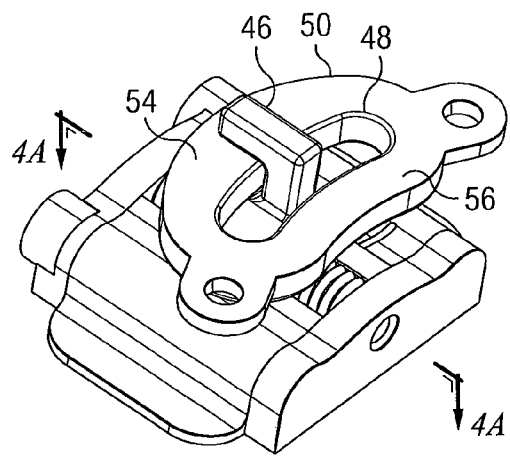
FIG. 5A
FIG. 5B
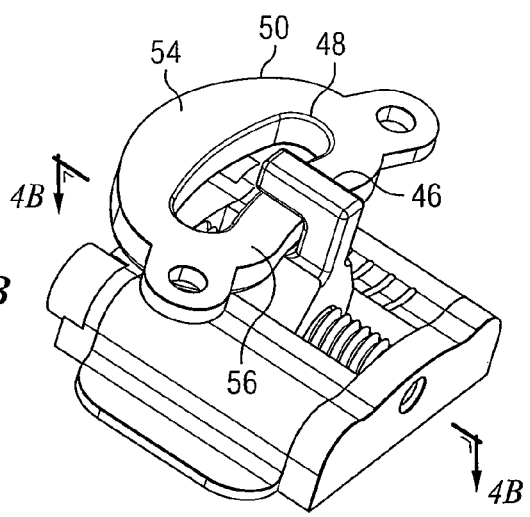

ORAL APPLIANCE FOR TREATING A BREATHING CONDITION

CROSS-REFERENCE TO RELATED APPLICATION

This application is a continuation of U.S. application Ser. No. 11/278,918 filed Apr. 6, 2006 and entitled "Oral Appliance for Treating a Breathing Condition."

TECHNICAL FIELD OF THE INVENTION

This invention relates generally to oral appliances, and more particularly to an oral appliance for use in treating a breathing condition.

BACKGROUND

Many people experience breathing problems, which may result in difficulty sleeping, in snoring, or in other more serious conditions such as obstructive sleep apnea. One treatment for such breathing disorders involves the use of devices that are inserted into a user's mouth for extending the user's lower jaw forward. These devices open the airway (i.e., breathing passageway) more fully to allow easier breathing through the nose and mouth. Certain of these devices include upper and lower arches that are connected together using a mechanism that may be adjusted to pull the lower arch, and thus the user's lower jaw, forward to open the airway more fully.

SUMMARY OF THE INVENTION

Oral appliances and methods according to the present invention may reduce or eliminate certain disadvantages and problems associated with previous devices and methods for improving breathing.

In one embodiment, an apparatus for use in treating a breathing condition includes a body for coupling to an upper dental arch, a threaded member, a hook, a receiver configured to be coupled to a lower dental arch, and an extender configured to be coupled to the receiver. The body comprises a front stop, a rear stop, and a guide extending between the front stop and rear stop. The threaded member is configured to be coupled between the front stop and rear stop of the body and is configured to rotate relative to the body. The hook is configured to be coupled to the guide, comprises a threaded passage configured to engage the threaded member, and comprises an arm configured to engage the lower dental arch. The hook is configured to travel in a forward direction along the guide between the front stop and rear stop of the body in response to rotational adjustment of the threaded member to adjust the lower dental arch to an optimum position in the forward direction for a particular user's anatomy and breathing condition. The receiver comprises a shelf extending in a rearward direction opposite the forward direction and is configured to engage the arm of the hook. The extender provides a shelf that is more rearward than the shelf of the receiver such that engagement of the shelf of the extender provides additional extension of the lower dental arch in the forward direction relative to engagement of the shelf of the receiver.

In another embodiment, an apparatus for use in treating a breathing condition includes a body for coupling to an upper dental arch, a threaded member, a hook, a receiver configured to be coupled to a lower dental arch, and a post configured to be coupled to the body. The body comprises a front stop, a rear stop, and a guide extending between the front stop and rear stop. The threaded member is configured to be coupled between the front stop and rear stop of the body and is configured to rotate relative to the body. The hook is configured to be coupled to the guide, comprises a threaded passage configured to engage the threaded member, and comprises an arm configured to engage the lower dental arch. The hook is configured to travel in a forward direction along the guide between the front stop and rear stop of the body in response to rotational adjustment of the threaded member to adjust the lower dental arch to an optimum position in the forward direction for a particular user's anatomy and breathing condition. The receiver comprises a shelf extending in a rearward direction opposite the forward direction and is configured to engage the arm of the hook. The post extends in a forward direction and is configured to couple the apparatus to another device for use in treating a breathing condition. The post has a substantially oval-shaped transverse cross-section configured to limit the rotation of the other device when the other device is coupled to the post In another embodiment, an oral appliance for treating a breathing condition includes an upper dental arch configured to receive at least some of a user's upper teeth and a lower arch configured to receive at least some of the user's lower teeth. The upper dental arch includes a connector. The lower arch includes a posterior surface configured to face in an anatomically posterior direction when the user's lower teeth are received in the lower dental arch; a recess in the posterior surface, the recess configured to be open to the anatomically posterior direction; and a removable receiver configured to be positioned within the recess and to be engaged by the connector to define the forward position of the lower dental arch relative to the upper dental arch.

In another embodiment, a removable receiver for use in constructing an oral appliance for treating a breathing condition is configured to be removably positioned within a recess in a posterior surface of a lower dental arch configured to receive at least some of a user's lower teeth, the posterior surface configured to face in an anatomically posterior direction when the user's lower teeth are received in the lower dental arch, the recess configured to be open to the anatomically posterior direction. The removable receiver is configured to be engaged by a connector of an upper dental arch configured to receive at least some of the user's upper teeth, such that engagement defines the forward position of the lower dental arch relative to the upper dental arch.

In another embodiment, a kit for use in constructing an oral appliance for treating a breathing condition includes a plurality of removable receivers. Each of the plurality of removable receivers is configured to be removably positioned within a recess in a posterior surface of a lower dental arch configured to receive at least some of a user's lower teeth, the posterior surface configured to face in an anatomically posterior direction when the user's lower teeth are received in the lower dental arch, the recess configured to be open to the anatomically posterior direction. Each of the plurality of removable receivers is configured to be engaged by a connector of an upper dental arch configured to receive at least some of the user's upper teeth, such that engagement defines the forward position of the lower dental arch relative to the upper dental arch. Each of the plurality of removable receivers differs in length from other removable receivers in the plurality of removable receivers such that a particular removable receiver in the plurality of removable receivers may be selected to be positioned within the recess according to a particular user's anatomy and breathing condition.

In another embodiment, a method of assembling an apparatus for use in improving a user's breathing includes selecting and removably positioning a particular one of a plurality of removable receivers. The particular one of the plurality of removable receivers is selected according to a particular user's anatomy and breathing condition. Each removable receiver of the plurality of removable receivers is configured to be removably positioned within a recess in a posterior surface of a lower dental arch configured to receive at least some of a user's lower teeth, the posterior surface configured to face in an anatomically posterior direction when the user's lower teeth are received in the lower dental arch, the recess configured to be open to the anatomically posterior direction. Each removable receiver of the plurality of removable receivers is configured to be engaged by a connector of an upper dental arch configured to receive at least some of the user's upper teeth, such that engagement defines the forward position of the lower dental arch relative to the upper dental arch. Each removable receiver of the plurality of removable receivers differs in length from other removable receivers in the plurality of removable receivers. The selected one of the plurality of removable receivers is removably positioned within the recess.

In another embodiment, a method of improving a user's breathing includes inserting an upper dental arch into the user's mouth such that the upper dental arch receives at least some of the user's upper teeth, the upper dental arch comprising a hook, an adjustor, an adjustment key, and a front plate, the adjustment key comprising a retaining ring that prevents the adjustment key from being removed while the front plate is secured to the upper dental arch; inserting a lower dental arch into the user's mouth such that the lower dental arch receives at least some of the user's lower teeth; coupling the upper dental arch to the lower dental arch by engaging the lower dental arch with the hook; adjusting the forward position of the lower dental arch relative to the upper dental arch by rotating the adjustor with the adjustment key; removing the front plate from the upper dental arch; removing the adjustment key; and recoupling the front plate to the upper dental arch without the adjustment key.

Certain embodiments of the present invention may provide one or more technical advantages. For example, certain embodiments may provide for precise positioning of the lower jaw as well as positioning of one or more devices relative to the upper dentition. As another example, certain embodiments may provide for improved positioning of the lower arch relative to the upper arch for particular users. Certain embodiments may provide for improved positioning or coupling of an oral appliance to a breathing device. Certain embodiments may provide some, none, or all of these advantages. Certain embodiments may provide one or more other technical advantages, one or more of which may be readily apparent to those skilled in the art from the figures, description, and claims included herein.

BRIEF DESCRIPTION OF THE DRAWINGS

For a more complete understanding of the present invention and at least some of its advantages, reference is now made to the following description taken in conjunction with the accompanying drawings, in which:

FIGS. 2A through 5B illustrate an example adjustment mechanism;

DESCRIPTION OF EXAMPLE EMBODIMENTS

Figure 1:
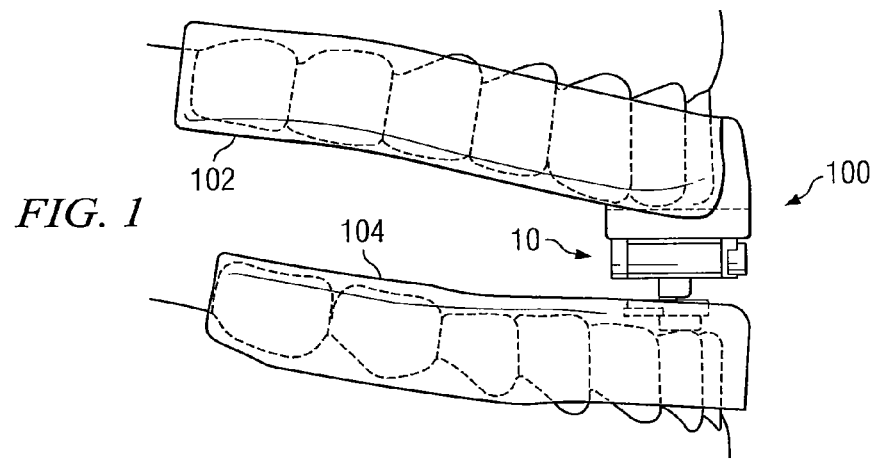
FIG. 1 illustrates an example oral appliance for improving a user's breathing.
Figure 2A:
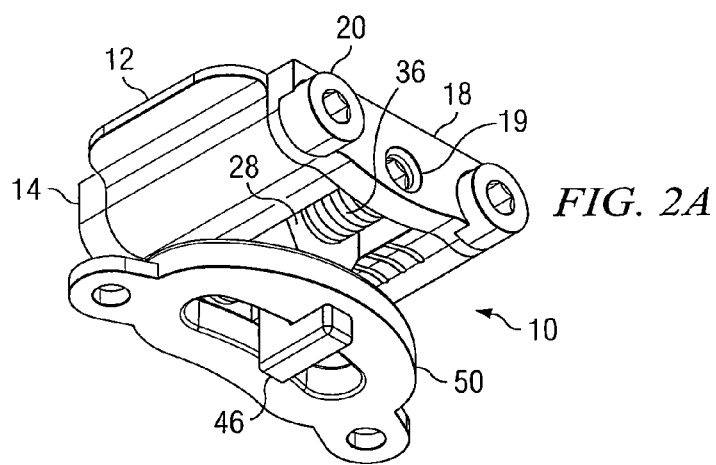
Figure 2B:
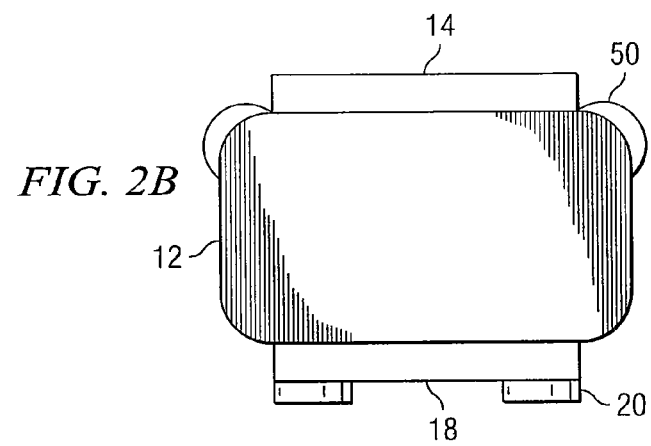
Figure 2C:
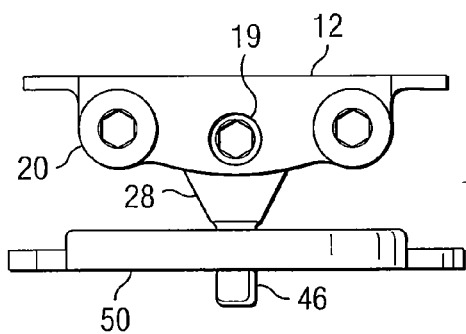
Figure 2D:
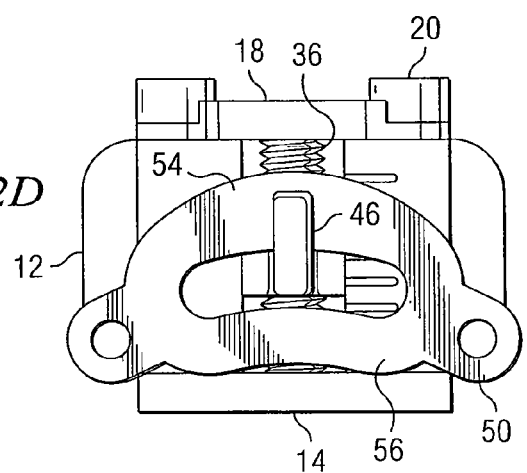
Figure 3:
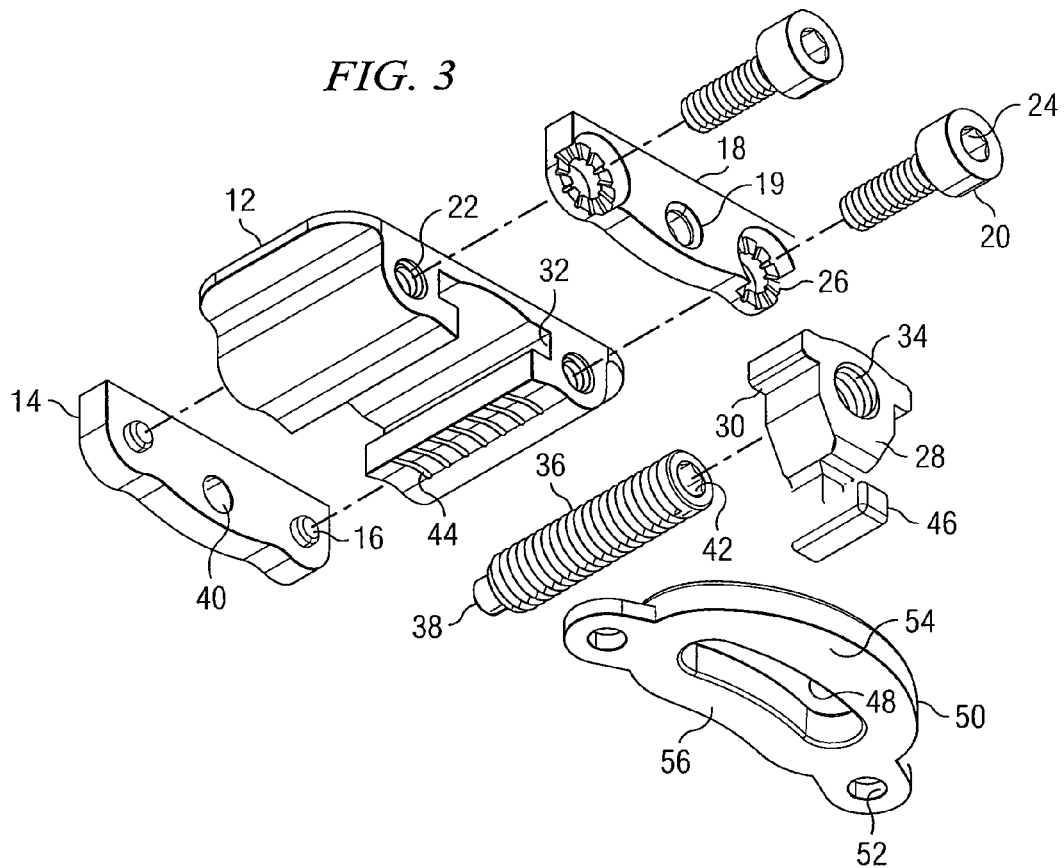

FIG. 1 illustrates an example oral appliance 100 for improving a user's breathing. In general, oral appliance 100 may be used to treat sleep disordered breathing, such as snoring or obstructive sleep apnea, through forward adjustment of the user's lower jaw relative to the upper jaw. This forward adjustment opens the breathing passage more fully and facilitates improved breathing through the user's nose and mouth. In certain embodiments, oral appliance 100 remains entirely within the user's mouth and surfaces of oral appliance 100 that may contact the interior of the user's mouth are smooth to prevent injury or discomfort.

Oral appliance 100 includes an upper arch 102 configured to receive at least some of a user's upper teeth, a lower arch 104 configured to receive at least some of the user's lower teeth, and an adjustment mechanism 10. Upper arch 102 and lower arch 104 may include molds of at least some of the user's upper and lower teeth, respectively, for improved performance and comfort. Adjustment mechanism 10 couples lower arch 104 to upper arch 102 and may be adjusted to pull lower arch 104 forward to facilitate improved breathing. In certain embodiments, adjustment mechanism 10 may also vertically position lower arch 104 relative to upper arch 102 to determine the opening of the user's lower jaw. The components of adjustment mechanism 10 may be made from any suitable material such as, for example, a biocompatible metal or hard plastic.

FIGS. 2A through 5B illustrate an example adjustment mechanism 10 for use with oral appliance 100. In certain embodiments, adjustment mechanism 10 may include body 12, hook 28, adjustor 36, and receiver 50. Body 12 may be integrated into or coupled to upper arch 102. Body 12 may include a rear plate 14, one or more rear fasteners 16, a front plate 18, and one or more front fasteners 20. In certain embodiments, body 12 may further include one or more fastener passages 22, one or more guides 32, and one or more adjustment indicators 44. Hook 28 may include flange 30, adjustor passage 34, and arm 46.

When assembled, rear plate 14 may be coupled to body 12 through the use of one or more fasteners 16. Fasteners 16 may be threaded fasteners, pins, or any other appropriate fastener to couple rear plate 14 to body 12. Hook 28 may be coupled to body 12 through the use of one or more flanges 30 engaged within the one or more guides 32. Adjustor 36 may include pin 38 and opening 42. Opening 42 may be square, hexagonal, or any other appropriate shape to allow for a rotational force to be applied to adjustor 36. Adjustor 36 may be positioned within adjustor passage 34 of hook 28 and pin 38 may be aligned with and inserted into hole 40 of rear plate 14.

Front plate 18 may be coupled to body 12 through the use of one or more fasteners 20. Fasteners 20 may include threaded fasteners, pins, or any other appropriate fastener to couple front plate 18 to body 12. In certain embodiments, front plate 18 may include one or more structures to lock or secure one or more fasteners 20. For example, in embodiments utilizing a threaded fastener 20 as shown, front plate 18 may include one or more grooves and associated projections 26 to better secure fastener 20 in place.

In certain embodiments, front plate 18 may include an opening 19 that substantially aligns with opening 42 of adjustor 36. In operation, opening 19 may provide access to opening 42 of adjustor 36 for locational adjustment of hook 28. In certain embodiments, adjustor 36 may be threaded and may engage cooperative threads of adjustor passage 34 of hook 28 such that rotation of adjustor 36 moves hook 28 forward or rearward relative to body 12.

Receiver 50 is configured to receive arm 46 of hook 28 such that forward adjustment of hook 28 pulls lower arch 104 forward. Receiver 50 may be fully integrated into, permanently coupled to, or separate and removable from lower arch 104. In certain embodiments, receiver 50 may include one or more openings 52 that may be used to couple receiver 50 to lower arch 104 through the use of any appropriate fastener. In certain embodiments, receiver 50 may also include slot 48 separating front shelf 54 from rear shelf 56. In operation, hook 28 may engage either front shelf 54 or rear shelf 56. In certain embodiments, the use of rear shelf 56 may provide additional extension of lower arch 104 in the forward direction relative to the use of front shelf 54.

Receiver 50 may be modified according to particular needs to provide increased flexibility. For example, the vertical location of front shelf 54 and/or rear shelf 56 relative to lower arch 104 may be adjusted or otherwise modified, either during or after initial construction of receiver 50. As another example, receivers 50 with varying vertical dimensions may be provided, such that the use of a particular receiver 50 may be selected to define a prescribed vertical separation between upper arch 102 and lower arch 104 and thus a prescribed opening of the user's lower jaw. As another example, the vertical location of front shelf 54 and/or rear shelf 56 may be selected by coupling receiver 50 to lower arch 104 in either of two possible orientations (i.e., with a particular horizontal surface facing up or facing down). As another example, receivers 50 with varying horizontal dimensions may be provided, such that the use of a particular receiver 50 may be selected to define a prescribed forward location (or range of locations) for lower arch 104 relative to upper arch 102.

Slot 48 may allow horizontal movement of lower arch 104 relative to lower upper 102 when lower arch 104 is coupled to upper arch 102. Similarly, the posterior surface of front shelf 54 and/or rear shelf 56 may be shaped to guide the horizontal movement of lower arch 104 relative to upper arch 102 in an arc-shaped or other desirable path.

Figure 6A:
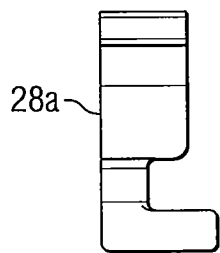
FIGS. 6A through 6C illustrate example hooks with varying lengths, for use with an example adjustment mechanism.
Figure 6B:
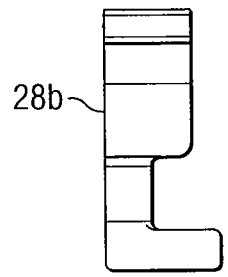
Figure 6C:
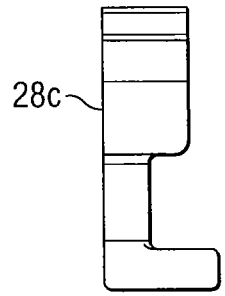

FIGS. 6A through 6C illustrate example hooks 28 with varying lengths, for use with adjustment mechanism 10. In operation, the use of a particular hook 28 may be selected to define a prescribed vertical separation between upper arch 102 and lower arch 104 and thus a prescribed opening of the user's lower jaw. For example, in the embodiments shown, the use of hook 28c may allow for greater vertical separation between upper arch 102 and lower arch 104 than the vertical separation allowed with the use of hooks 28a or 28b. In particular embodiments, the use of hooks 28 with varying lengths, together with the use of receivers 50 with varying vertical dimensions, may provide an increased range and/or precision for selection of a prescribed opening of the user's lower jaw.

Figure 7A:
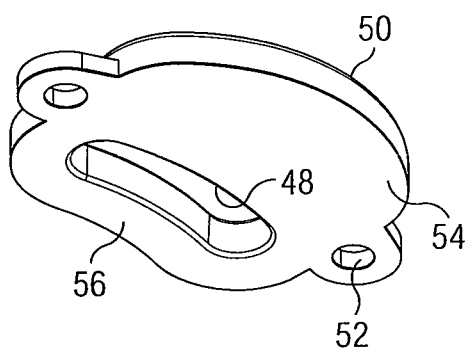
FIGS. 7A through 7C illustrate example receivers with varying dimensions.
Figure 7B:
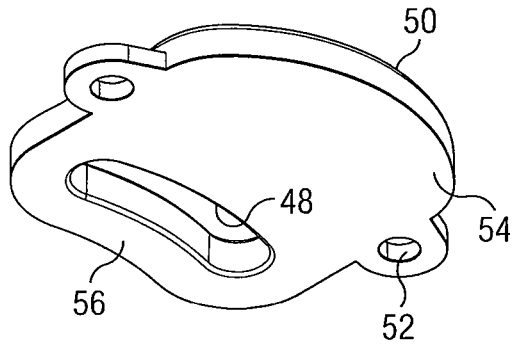
Figure 7C:
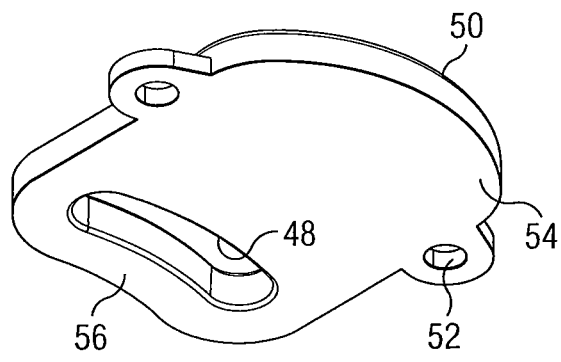
Figure 8A:
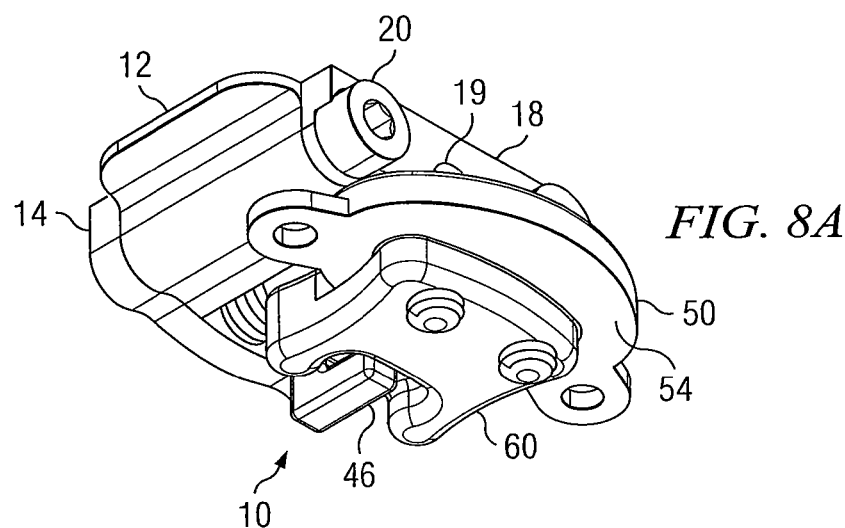
FIGS. 8A through 10 illustrate an example adjustment mechanism utilizing an example extender.
Figure 8B:
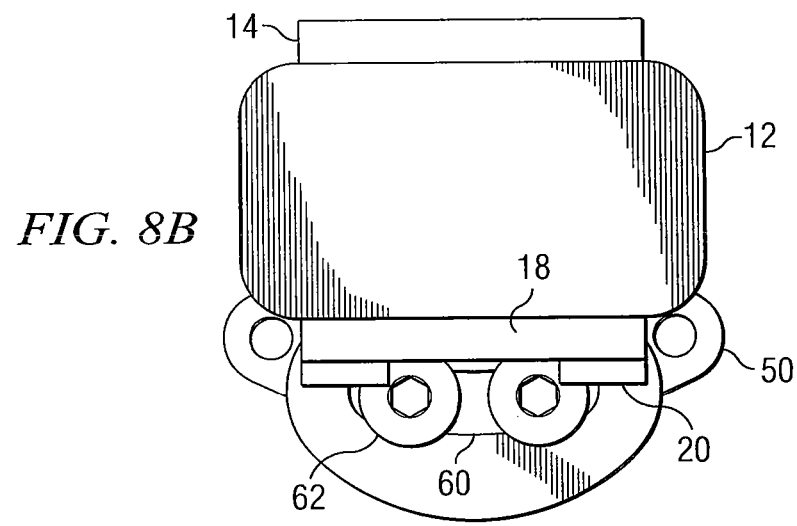
Figure 8C:
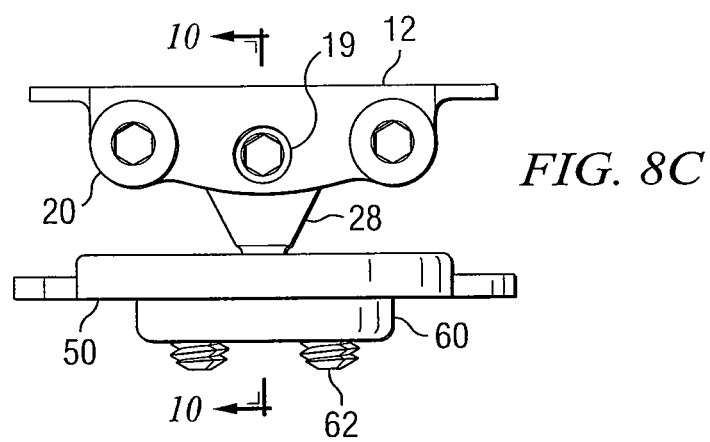
Figure 8D:
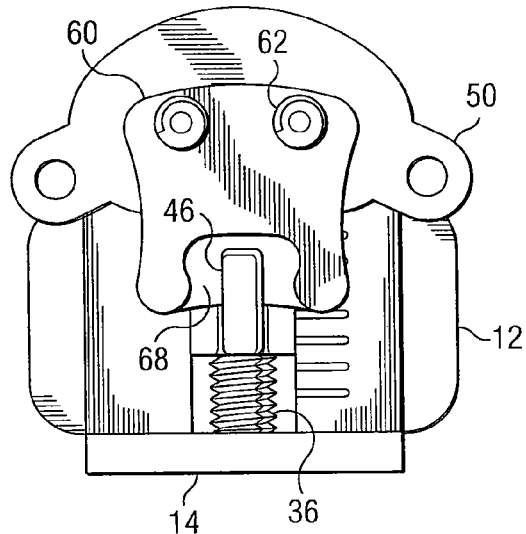
Figure 9:
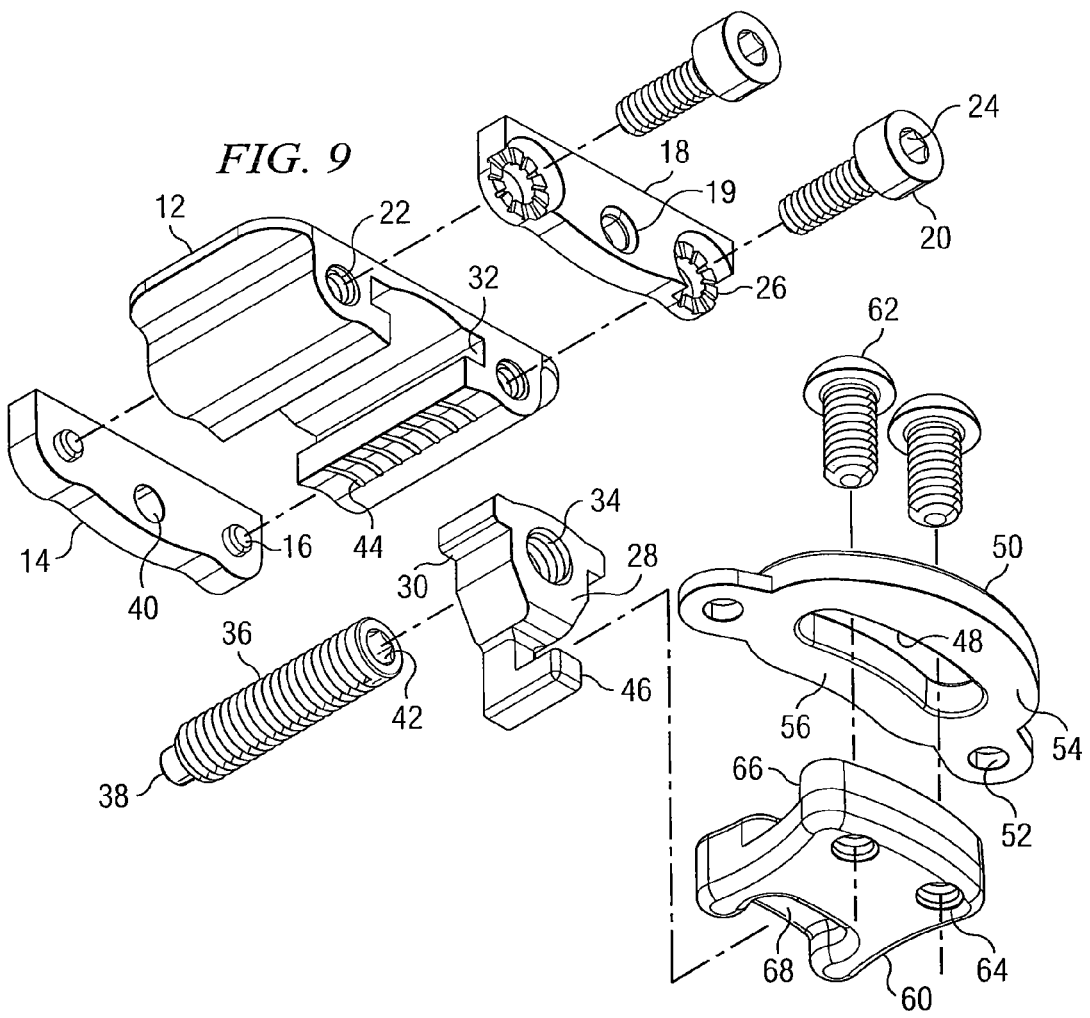
Figure 10:
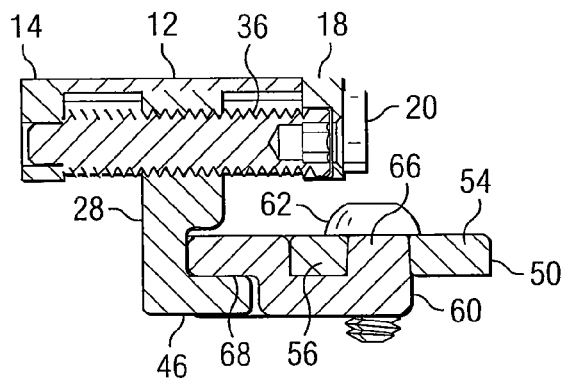

FIGS. 7A through 7C illustrate example receivers with varying dimensions, for use with adjustment mechanism 10. In operation, the use of a particular receiver may be selected to define a prescribed forward location (or range of forward locations) for lower arch 104 relative to upper arch 102 and thus a prescribed forward location (or range of forward locations) for the user's lower jaw. For example, in the embodiments shown, the use of receiver 50c may allow for lower arch 104 to be positioned further forward with respect to upper arch 102 than with the use of receivers 50a or 50b. In particular embodiments, the use of receivers 50 with varying dimensions may provide an increased range and/or precision for adjusting the forward location of lower arch 104 relative to upper arch 102.

FIGS. 8A through 10 illustrate an example adjustment mechanism 10 utilizing an example extender 60. In certain embodiments, extender 60 couples to receiver 50 and operates to receive arm 46 of hook 28 such that the forward positioning of lower arch 104 is greater than that provided without extender 60.

Figure 11A:
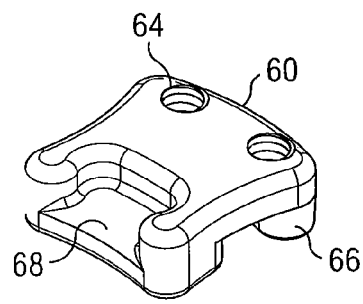
FIGS. 11A and 11B illustrate an example extender.
Figure 11B:
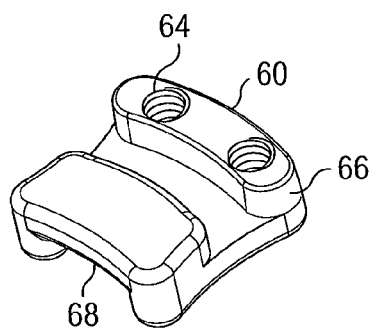

FIGS. 11A and 11B illustrate an example extender 60 for use with an example adjustment mechanism 10. In certain embodiments, extender 60 may include a shelf 68 that engages arm 46 of hook 28. In certain embodiments, extender 60 may also include one or more projections 66 that may cooperatively engage slot 48 of receiver 50. In certain embodiments, extender 60 may also include one or more openings 64 that may cooperate with one or more fasteners 62 to couple extender 60 to receiver 50, such as via slot 48. Fastener 62 may be a threaded fastener, pin, or any other appropriate fastener for coupling extender 60 to receiver 50.

Figure 12A:
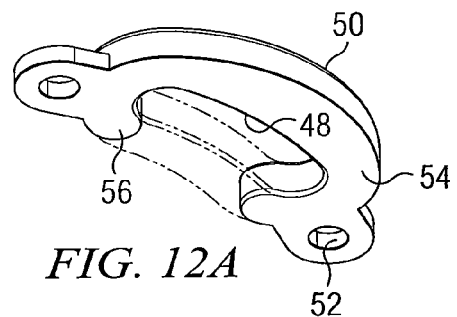
FIGS. 12A and 12B illustrate example receivers.
Figure 12B:
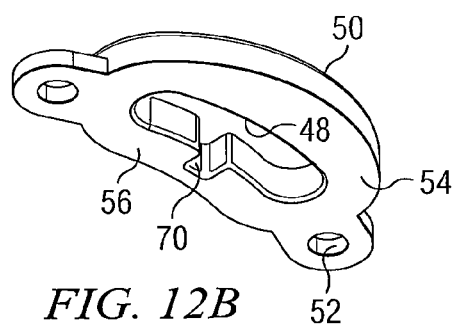

FIGS. 12A and 12B illustrate example receivers 50 for use with example adjustment mechanisms 10. As shown in FIG. 12A, in certain embodiments, receiver 50 may include only a single shelf 54, in which case slot 48 may be fully or partially exposed in the rearward direction. As shown in FIG. 12B, receiver 50 may include notch 70 in slot 48. In operation, the use of receiver 50 including only a single shelf 54 or including notch 70 may allow hook 28 to engage or disengage from shelf 54 of receiver 50 after oral appliance 100 has been inserted into a user's mouth.

Figure 13:
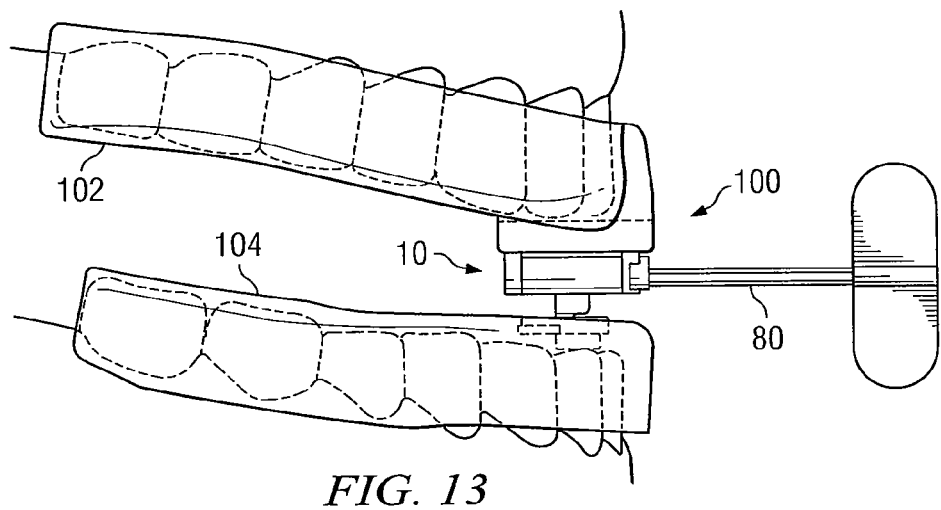
FIGS. 13 through 16 illustrate an example adjustment mechanism utilizing an example adjustment key.

FIG. 13 illustrates an example oral appliance 100 with an example adjustment key 80. Adjustment key 80 may have a cross-section that is hexagonal, square, or any other appropriate shape. In certain embodiments, adjustment key 80 may be used to exert a rotational force on adjustor 36 causing adjustor 36 to turn and thereby provide adjustment of hook 28, forward or rearward.

Figure 15:
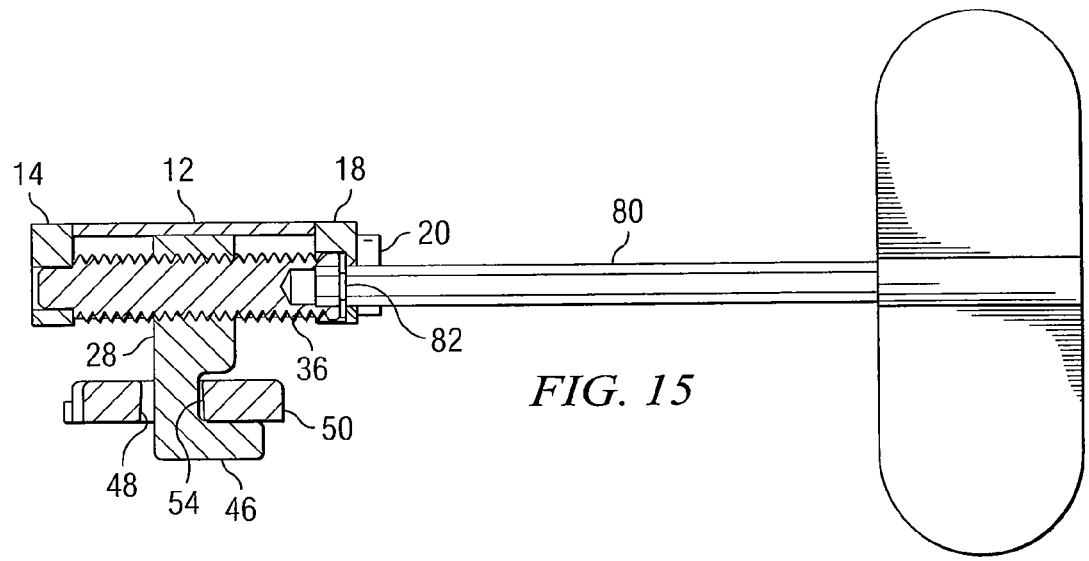
Figure 14:
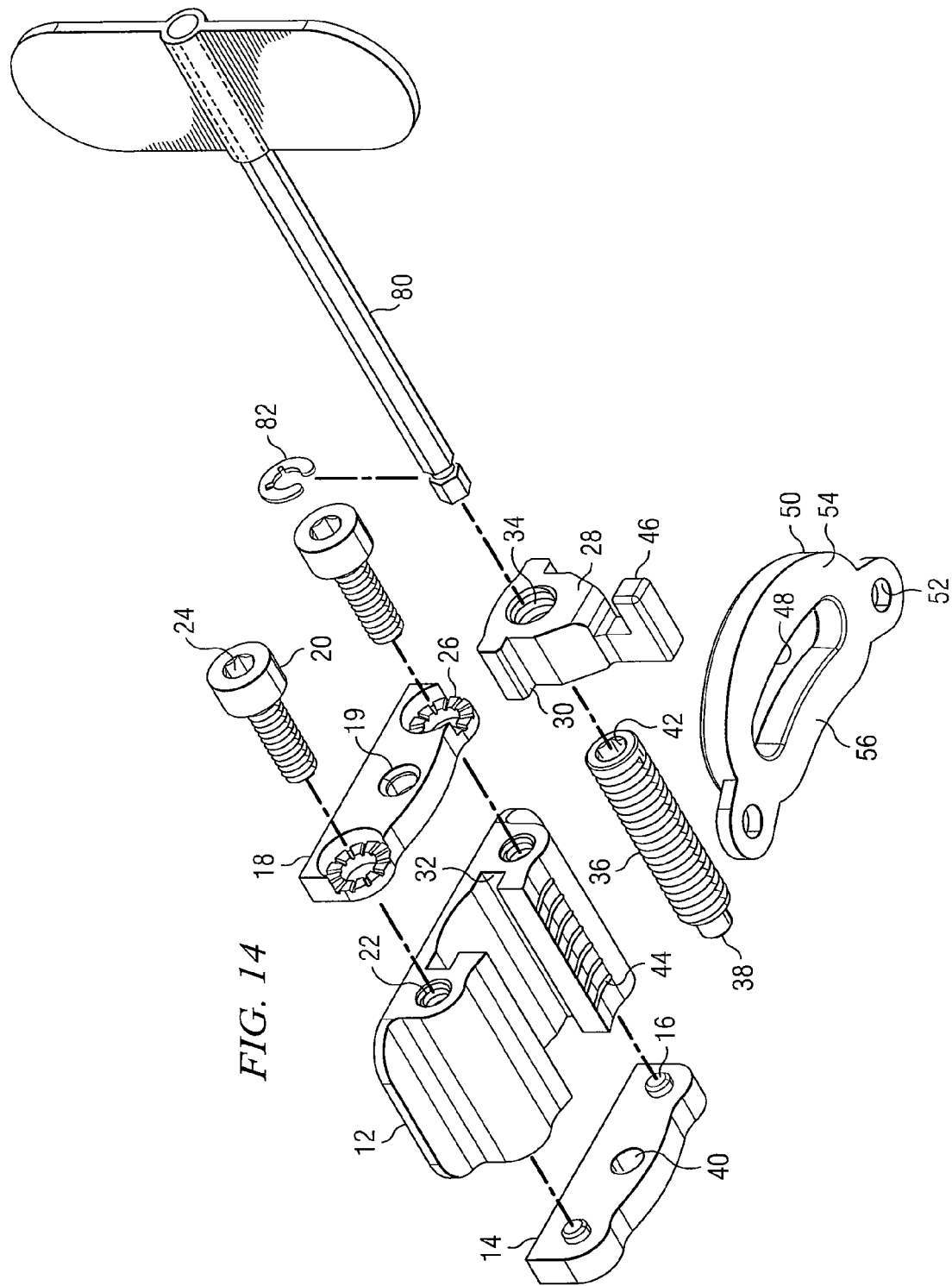
Figure 16:
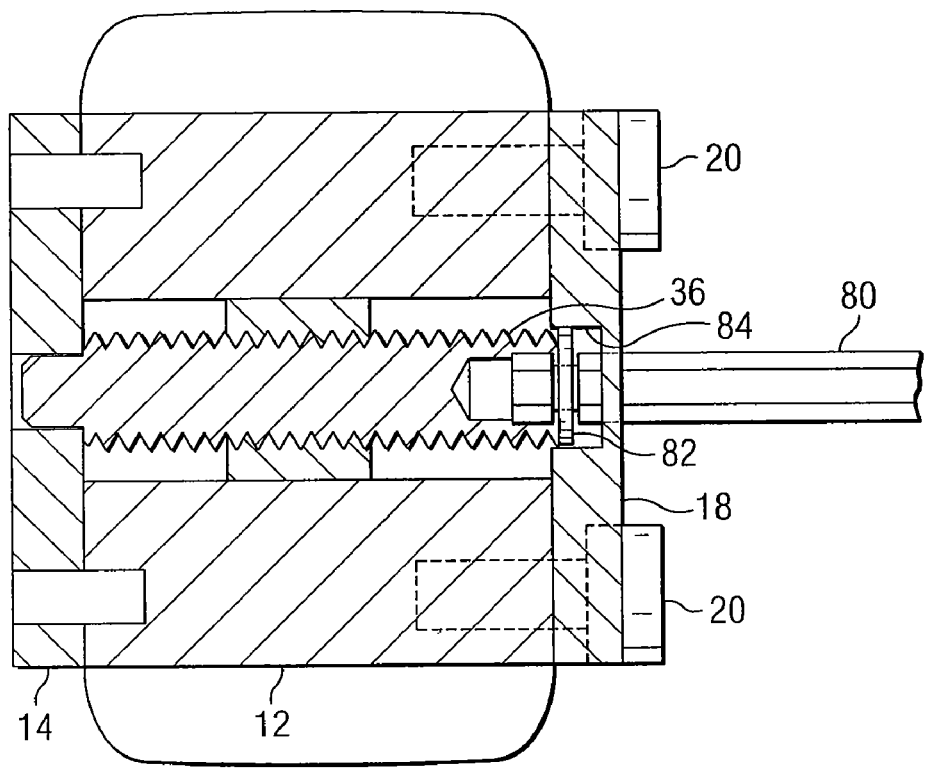
Figure 17:
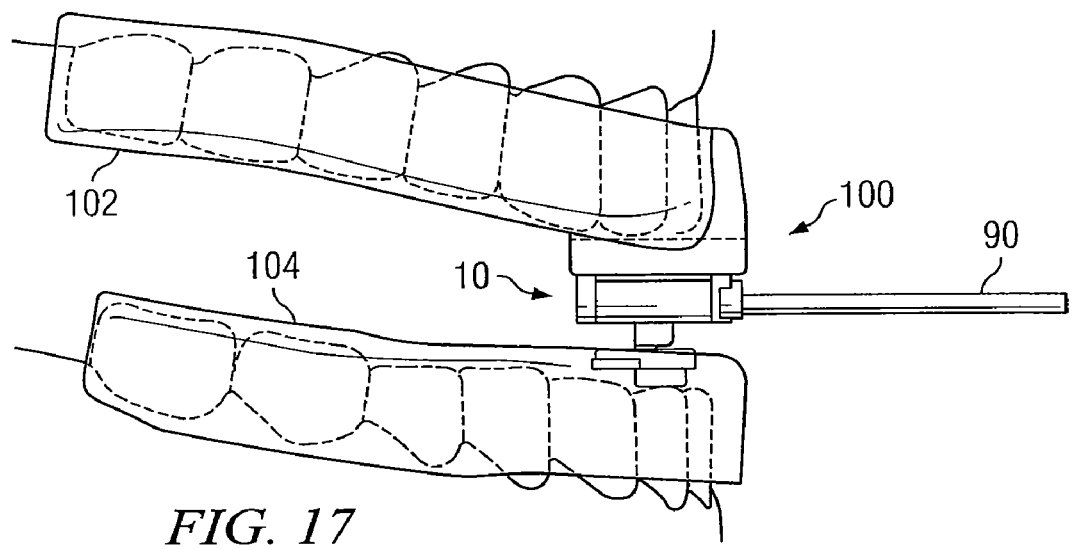
FIGS. 17 through 19B illustrate an example adjustment mechanism utilizing an example extension post.
Figure 18:
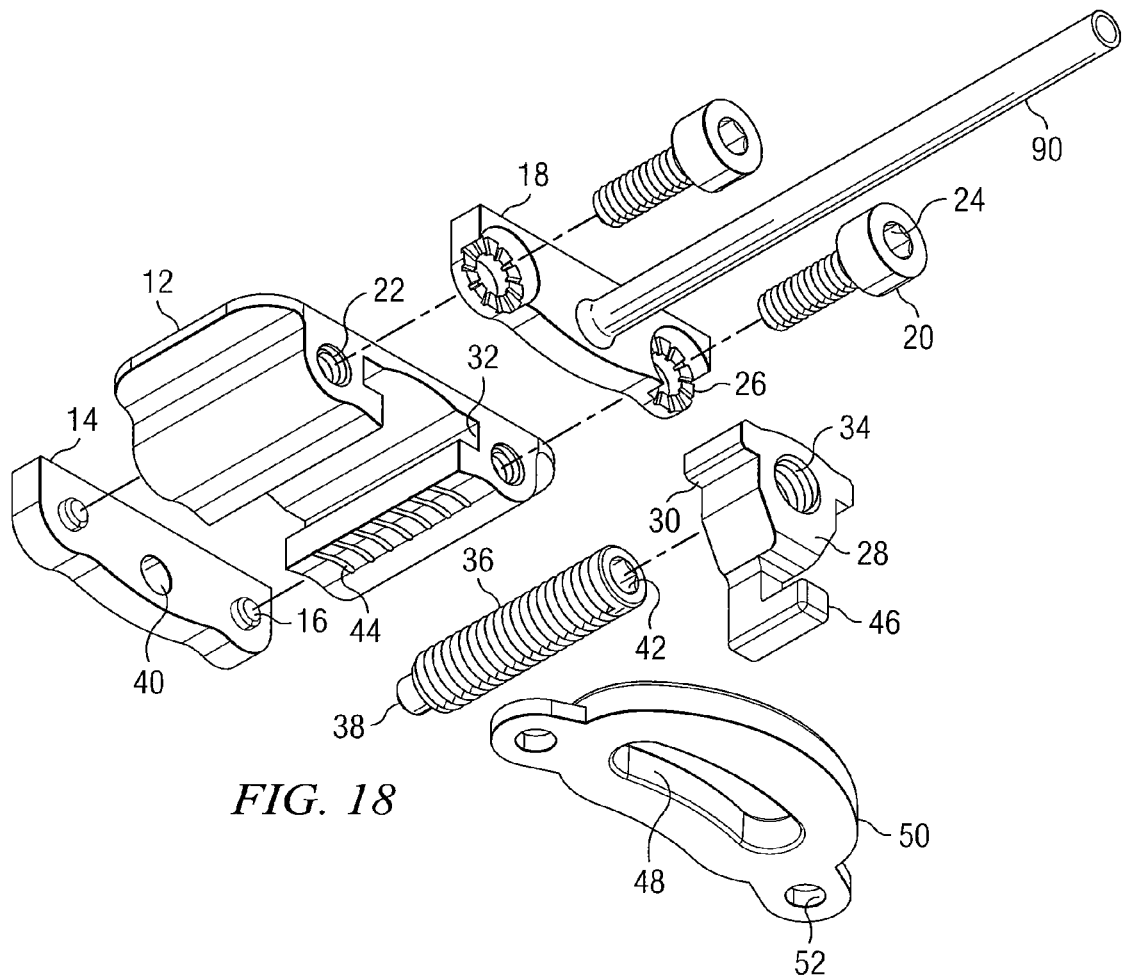

FIGS. 14 through 16 illustrate example adjustment mechanisms 10 utilizing example adjustment keys 80. In certain embodiments, adjustment key 80 may be coupled to adjustment mechanism 10 through the use of retainer ring 82 and notch 84. In operation, retainer ring 82 may engage notch 84, thus preventing removal of adjustment key 80. In operation, embodiments of adjustment mechanism 10 including adjustment key 80 and retaining ring 82 may be used by a particular user during a trial period for oral appliance 100. During this trial period, the user and/or a clinician may make periodic adjustments to adjustment mechanism 10 through the use of adjustment key 80 to achieve the desired positioning of lower arch 104 relative to upper arch 102. In these embodiments, once the desired positioning has been achieved, adjustment key 80 and retaining ring 82 may be removed. In these embodiments, once the desired positioning has been achieved, front plate 18 may be replaced with a front plate 18 that does not include an opening 19.

FIGS. 17 through 19B illustrate an example oral appliance 100 with an example extension post 90. Extension post 90 may be formed of any suitable material, such as a metal or hard plastic. In certain embodiments, extension post 90 may be used to couple oral appliance 100 to one or more other devices and/or to orient one or more other devices relative to oral appliance 100. For example, extension post 90 may be used to couple oral appliance 100 to a breathing device, such as a venting seal, a face mask, or a nose mask. In a particular embodiment, extension post may be used to couple oral appliance 100 to a mask associated with a continuous positive airway pressure (CPAP) system.

In certain embodiments, extension post 90 may be substantially rigid, to provide for sufficiently precise positioning of one or more devices relative to upper arch 102. For example, in certain embodiments, extension post 90 may be used to provide substantially precise and repeatable positioning of a face mask or nose mask relative to upper arch 102. The length of extension post 90 may vary depending upon its intended use. For example, extension post 90 may be substantially shorter if it is intended to be used to couple a venting seal to oral appliance 100 than if it is intended to couple a nose mask to oral appliance 100. The invention contemplates any reasonable length of extension post 90, so long as the length is appropriate to perform the intended function.

Figure 19A:
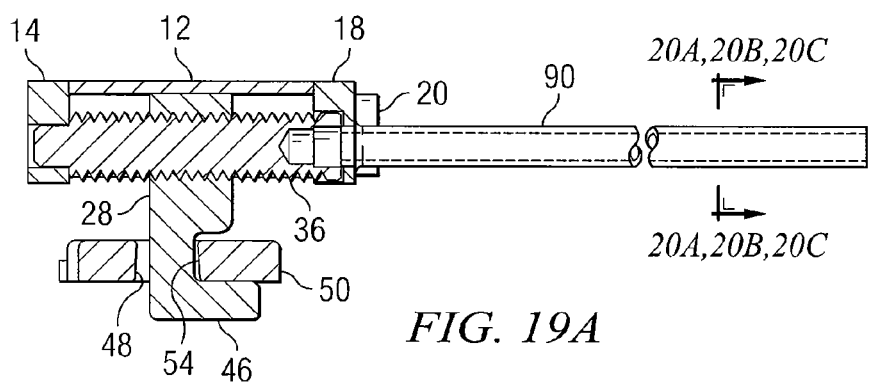
Figure 19B:
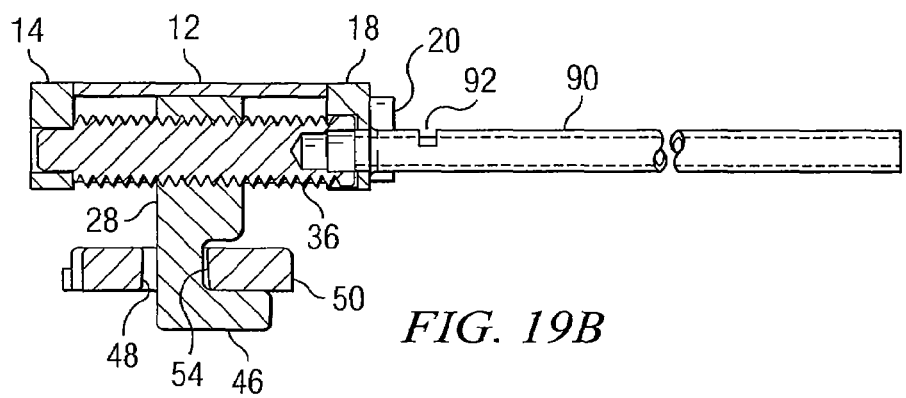

In certain embodiments, extension post 90 may include one or more features that can operate to index or assist in securing one or more devices to extension post 90. For example, as shown in FIG. 19B, extension post 90 may include one or more locators 92 at one or more positions along the length of extension post 90. In operation, a device coupled to or guided by extension post 90 may include one or more structures that can cooperate with the one or more locators 92 to index or assist in securing the device. In the embodiment shown, locator 92 is in the form of a notch, however, in alternative embodiments, locator 92 may be in the form of a ridge, protrusion, or any other appropriate shape or structure. In particular embodiments, the position of locator 92 may be adjustable.

In certain embodiments, extension post 90 may be coupled to front plate 18. In these embodiments, extension post 90 may be coupled through the use of any appropriate means, such as welding or threaded coupling. In alternative embodiments, extension post 90 may be integrally formed with front plate 18. In certain embodiments, extension post 90 may be substantially hollow and may couple to front plate 18 such that the hollow interior of extension post 90 substantially aligns with an opening 19. In operation, hollow portion 92 may provide access to adjustor 36 through opening 19. The cross-sectional shape of extension post 90 may take any appropriate form, so long as it remains reasonable for the intended function.

Figure 20A:
FIGS. 20A through 20B illustrate transverse cross-sectional views of example extension posts.
Figure 20B:
Figure 20C:

FIGS. 20A through 20C illustrate transverse cross-sectional views of example extension posts 90. As shown, extension post 90 may have a cross sectional shape that is a circle, oval, or diamond. In certain embodiments, non-circular cross-sections may function to more precisely position a device coupled to oral-appliance 100 through the use of extension post 90, by substantially limiting the likelihood that the device will rotate about the extension post 90.

In certain embodiments, receiver 50 may be removable. For example, lower arch 104 may include a recess that allows receiver 50 to be positioned within, and then removed from, lower arch 104. In embodiments including a removable receiver 50 and a recess in lower arch 104, the recess may be integrally formed in lower arch 104. In alternative embodiments, the recess may be formed in or by a housing that is included in lower arch 104.

Figure 21:
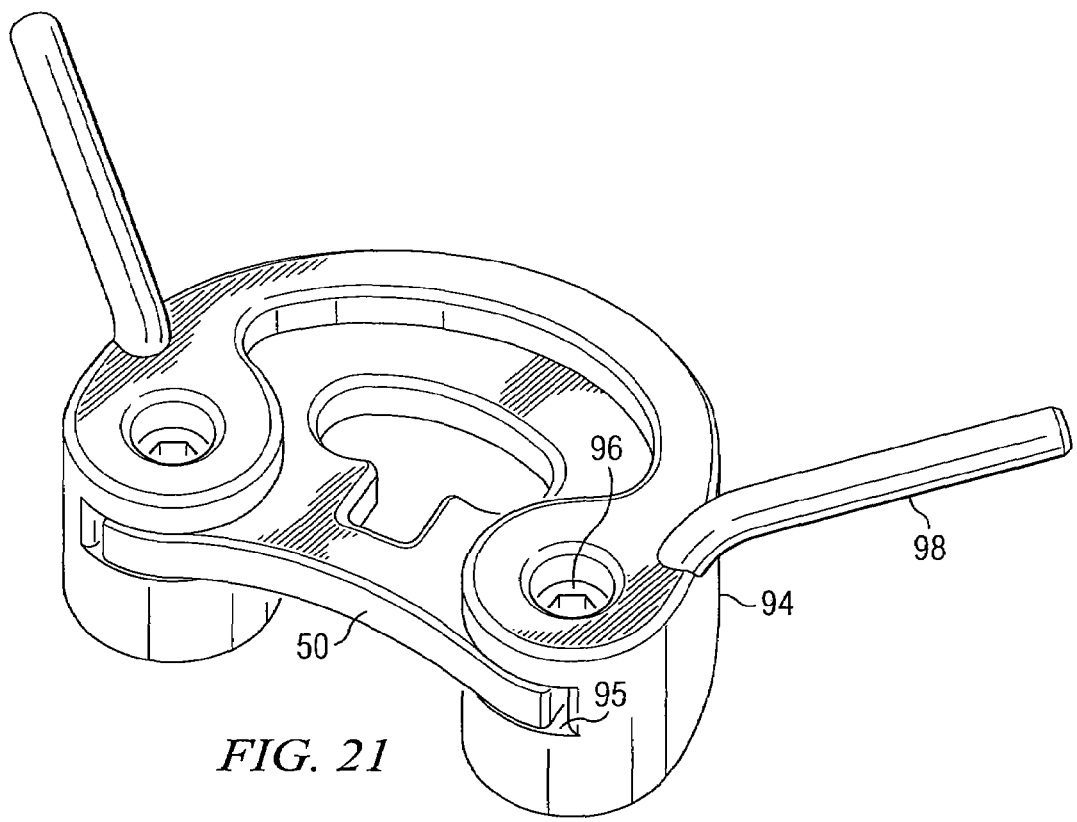
FIGS. 21 through 23 illustrate an example housing, for use with an example adjustment mechanism.
Figure 22:
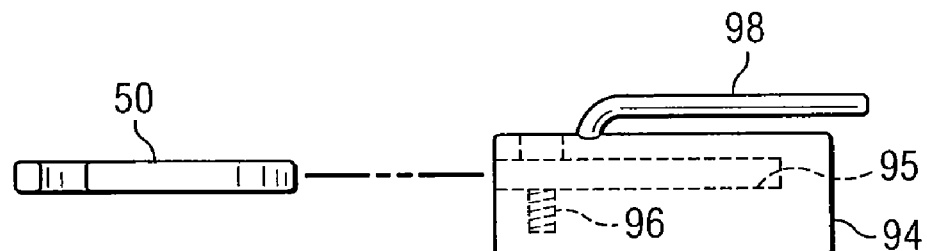
Figure 23:
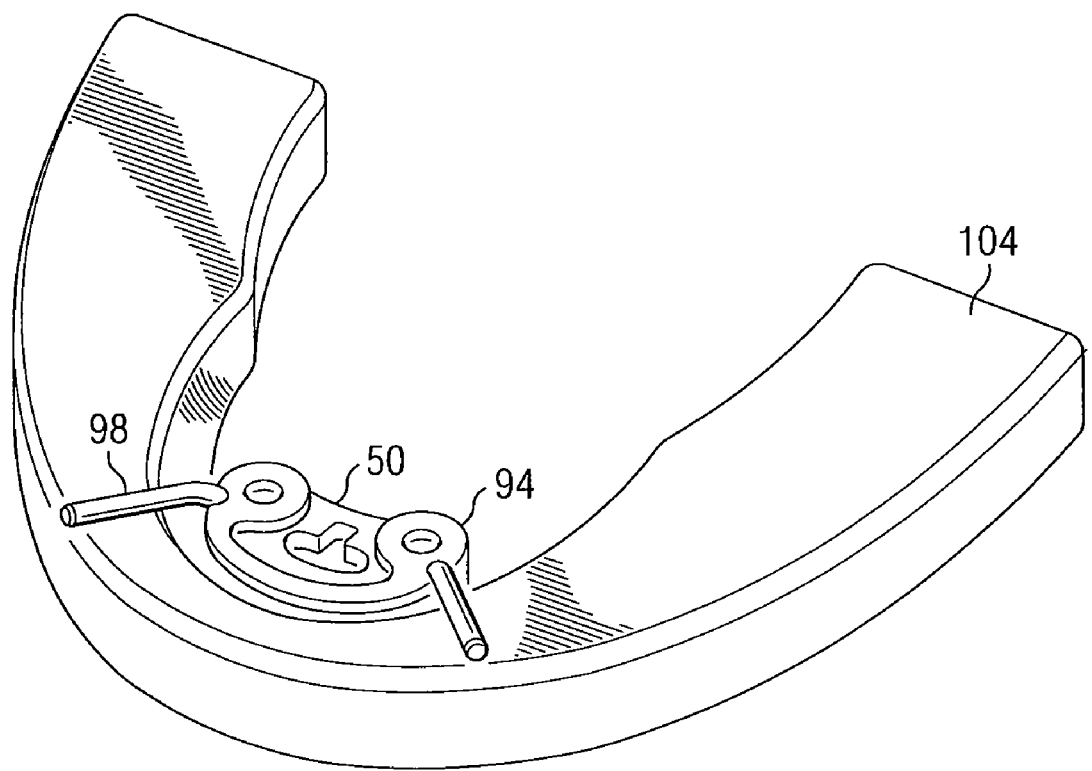

FIGS. 21 through 23 illustrate an example housing 94, for use with an example adjustment mechanism 10. In certain embodiments, adjustment mechanism 10 may include housing 94 to position and secure receiver 50. Housing 94 may be made of any appropriate material, such as metal or hard plastic. In certain embodiments, housing 94 may be integrally formed with lower arch 104. As shown, housing 94 may define recess 95 to accept receiver 50 within housing 94. In certain embodiments, housing 94 may include one or more fasteners 96 to secure receiver 50 within recess 95. In a particular embodiment, fastener 96 may be a threaded setscrew.

In certain embodiments, housing 94 may include one or more projections 98 that may be used to orient and/or secure housing 94 to lower arch 104. In particular embodiments, as in the example shown in FIG. 23, one or more projections 98 may be used to orient housing 94 to lower arch 104. In these embodiments, once housing 94 is properly oriented, housing 94 may be luted to (or otherwise secured to) lower arch 104. In certain embodiments, some or all of projections 98 may be removed before or after housing 94 is completely secured to lower arch 104.

FIGS. 24A through 25C illustrate example receivers 50, for use with an example housing 94. As shown, receiver 50 may have varying dimensions and the location of certain features of receiver 50 may vary. In operation, the use of a particular receiver 50 may be selected to define a prescribed forward location (or range of locations) for lower arch 104 relative to upper arch 102. For example, in the embodiments shown, the use of receiver 50f may allow for lower arch 104 to be positioned further forward with respect to upper arch 102 than with the use of receivers 50d and 50e. In particular embodiments, the use of receivers 50 with varying dimensions may provide an increased range and/or precision for adjusting the forward location of lower arch 104 relative to upper arch 102.

Figure 24A:
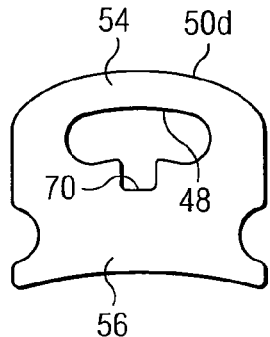
FIGS. 24A through 25C illustrate example receivers, for use with an example housing.
Figure 24B:
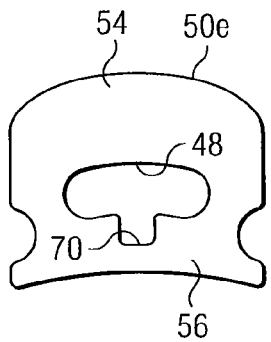
Figure 24C:
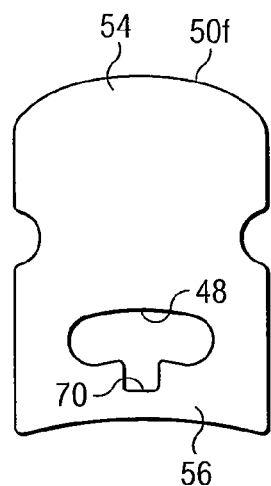
Figure 24D:
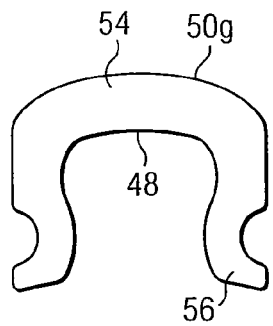

As shown in FIG. 24D, in certain embodiments, receiver 50 may include only a single shelf 54, in which case slot 48 may be fully or partially exposed in the rearward direction. In operation, the use of receiver 50 including only a single shelf 54 (or including notch 70) may allow hook 28 to engage or disengage from shelf 54 of receiver 50 after oral appliance 100 has been inserted into a user's mouth.

Figure 25A:
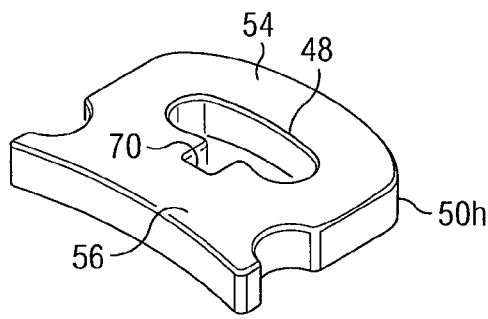
Figure 25B:
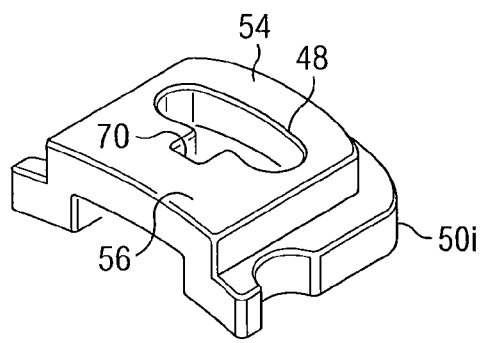
Figure 25C:
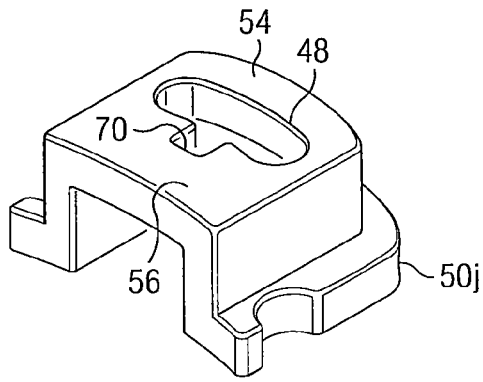

As shown in FIGS. 25A through 25C, receiver may have varying vertical dimensions. In operation, the use of a particular receiver 50 may be selected to define a prescribed vertical separation between upper arch 102 and lower arch 104 and thus a prescribed opening of the user's lower jaw. For example, in the embodiments shown, the use of receiver 50j may allow for greater vertical separation between upper arch 102 and lower arch 104 than the vertical separation allowed with the use of receivers 50h and 50i. In particular embodiments, the use of receivers 50 with varying vertical dimensions may provide an increased range and/or precision for selection of a prescribed opening of the user's lower jaw.

Figure 26:
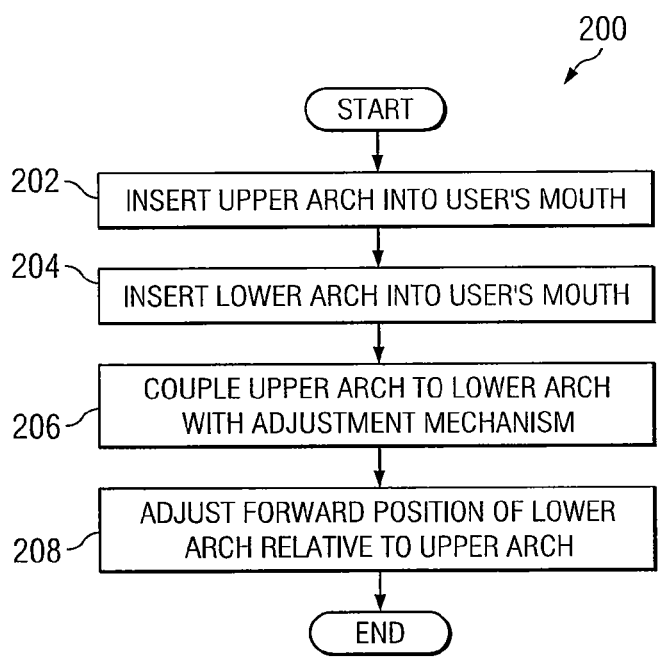
FIG. 26 illustrates an example method of improving a user's breathing.

FIG. 26 illustrates an example method of improving a user's breathing, indicated generally at 200. At step 202, upper arch 102 is inserted into the user's mouth. At step 204, lower arch is inserted into the user's mouth. At step 206, upper arch 102 is coupled to lower arch 104 by adjustment mechanism 10. In certain embodiments, adjustment mechanism 10 includes a body 12 coupled to upper arch 102, an adjustor 36, a hook 28, and a receiver 50 coupled to lower arch 104. In certain embodiments, upper arch 102 is coupled to lower arch 104 by engaging shelf 54 of receiver 50 with arm 46 of hook 28. In particular embodiments, the initial forward position of lower arch 104 relative to upper arch 102 is determined by engaging a particular one of multiple shelves 54 of receiver 50. In alternative embodiments, the initial forward position of lower arch 104 relative to upper arch 102 is determined by engaging shelf 68 of extender 60 coupled to receiver 50. At step 208, the forward position of lower arch 104 relative to upper arch 102 is adjusted to facilitate improved breathing by the user. In certain embodiments, the forward position is adjusted by rotating adjustor 36 using adjustment key 80 or in any other appropriate manner.

Although an example method is described, the steps may be accomplished in any appropriate order. For example, inserting the upper and lower arches can be accomplished sequentially, in any order, or simultaneously. As another example, upper arch 102 and lower arch 104 may be coupled subsequent to or prior to inserting upper arch 102 and lower arch 104 into the user's mouth. As another example, the adjustment of the forward position of lower arch 104 relative to upper arch 102 may be performed in measured increments interspersed with trial periods to test the effectiveness of the oral appliance in improving the user's breathing. Method 200 may include checking or verifying the forward position of lower arch 104 relative to upper arch 102 and then repeating step 208 as needed. The present invention contemplates using methods with additional steps, fewer steps, or different steps, so long as the methods remain appropriate for improving a user's breathing.

Although the present invention has been described in connection with several embodiments, it should be understood that a plenitude of changes, substitutions, variations, alterations, transformations, and modifications may be suggested to one of skill in the art, and it is intended that the present invention encompass such changes, substitutions, variations, alterations, transformations, and modifications as fall within the spirit and scope of the appended claims.

What is claimed is:

1. An oral appliance for treating a breathing condition, comprising:
    an upper dental arch configured to receive at least some of a user's upper teeth, the upper dental arch comprising a connector; and
    a lower dental arch configured to receive at least some of the user's lower teeth, the lower dental arch comprising:
        a posterior surface configured to face in an anatomically posterior direction when the user's lower teeth are received in the lower dental arch;
        a recess in the posterior surface, the recess configured to be open to the anatomically posterior direction; and
        a removable receiver configured to be removably positioned within the recess and to be engaged by the connector to define the forward position of the lower dental arch relative to the upper dental arch.

2. The oral appliance of claim 1, wherein the connector comprises:
    a body;
    a threaded member configured to be coupled to the body and to rotate relative to the body; and
    a hook comprising:
        a threaded passage configured to engage the threaded member; and
        an arm configured to engage the removable receiver;
    wherein the hook is configured to travel in a forward direction in response to rotational adjustment of the threaded member to adjust the lower dental arch to an optimum position in the forward direction for a particular user's anatomy and breathing condition.

3. The oral appliance of claim 2, wherein the body is integrated into the upper dental arch.

4. The oral appliance of claim 1, wherein the lower dental arch comprises a housing defining the recess.

5. The oral appliance of claim 4, wherein the housing comprises at least one fastener adapted to secure the removable receiver in the recess.

6. The oral appliance of claim 1, further comprising a post configured to couple the oral appliance to a venting seal, face mask, or nose mask.

7. A removable receiver for use in constructing an oral appliance for treating a breathing condition:
    the removable receiver configured to be removably positioned within a recess in a posterior surface of a lower dental arch configured to receive at least some of a user's lower teeth, the posterior surface configured to face in an anatomically posterior direction when the user's lower teeth are received in the lower dental arch, the recess configured to be open to the anatomically posterior direction;
    the removable receiver configured to be engaged by a connector of an upper dental arch configured to receive at least some of the user's upper teeth, such that engagement defines the forward position of the lower dental arch relative to the upper dental arch.

8. A kit for use in constructing an oral appliance for treating a breathing condition, the kit comprising a plurality of removable receivers each being:
    configured to be removably positioned within a recess in a posterior surface of a lower dental arch configured to receive at least some of a user's lower teeth, the posterior surface configured to face in an anatomically posterior direction when the user's lower teeth are received in the lower dental arch, the recess configured to be open to the anatomically posterior direction;
    configured to be engaged by a connector of an upper dental arch configured to receive at least some of the user's upper teeth, such that engagement defines the forward position of the lower dental arch relative to the upper dental arch; and
    differing in length from other removable receivers in the plurality of removable receivers such that a particular removable receiver in the plurality of removable receivers may be selected to be removably positioned within the recess according to a particular user's anatomy and breathing condition.

9. The kit of claim 8, further comprising a connector configured to be coupled to the upper dental arch, the connector comprising:
    a body;
    a threaded member configured to be coupled to the body and to rotate relative to the body; and
    a hook comprising:
        a threaded passage configured to engage the threaded member; and
        an arm configured to engage the selected removable receiver;
    wherein the hook is configured to travel in a forward direction in response to rotational adjustment of the threaded member to adjust the lower dental arch to an optimum position in the forward direction for the particular user's anatomy and breathing condition.

10. The kit of claim 8, further comprising a housing defining the recess.

11. The kit of claim 10, wherein the housing comprises at least one fastener configured to secure the selected removable receiver to the lower arch.

12. A method of assembling an apparatus for use in improving a user's breathing, comprising:

selecting, according to a particular user's anatomy and breathing condition, a particular one of a plurality of removable receivers, each removable receiver of the plurality of removable receivers being:

configured to be removably positioned within a recess in a posterior surface of a lower dental arch configured to receive at least some of a user's lower teeth, the posterior surface configured to face in an anatomically posterior direction when the user's lower teeth are received in the lower dental arch, the recess configured to be open to the anatomically posterior direction;

configured to be engaged by a connector of an upper dental arch configured to receive at least some of the user's upper teeth, such that engagement defines the forward position of the lower dental arch relative to the upper dental arch; and differing in length from other removable receivers in the plurality of removable receivers; and removably positioning the selected one of the plurality of removable receivers within the recess.

* * * * *